US006879713B1

(12) United States Patent
Keefe

(10) Patent No.: US 6,879,713 B1
(45) Date of Patent: Apr. 12, 2005

(54) MEIOTIC SPINDLE IMAGING IN OOCYTES AND USES THEREFOR IN IN VITRO FERTILIZATION

(75) Inventor: David L. Keefe, Newport, RI (US)

(73) Assignee: Women & Infants Hospital of Rhode Island, Providence, RI (US)

( * ) Notice: Subject to any disclaimer, the term of this patent is extended or adjusted under 35 U.S.C. 154(b) by 682 days.

(21) Appl. No.: 09/891,598

(22) Filed: Jun. 25, 2001

Related U.S. Application Data

(60) Provisional application No. 60/213,750, filed on Jun. 23, 2000.

(51) Int. Cl.$^7$ .................................................. G06K 9/00
(52) U.S. Cl. ........................ 382/128; 382/308; 382/321; 356/368; 356/39
(58) Field of Search .................................. 382/128, 129, 382/308, 321; 356/368, 39; 600/310; 128/922, 898; 250/363.02; 435/2; 800/14, 24; 377/10

(56) References Cited

U.S. PATENT DOCUMENTS

| | | | | |
|---|---|---|---|---|
| 5,231,464 A | * | 7/1993 | Ichimura et al. ............ 356/477 |
| 5,521,705 A | * | 5/1996 | Oldenbourg et al. ........ 356/368 |
| 5,982,535 A | * | 11/1999 | Inoue et al. ................. 359/394 |
| 6,062,225 A | | 5/2000 | Keefe et al. |
| 6,161,031 A | * | 12/2000 | Hochman et al. ........... 600/407 |
| 6,331,659 B1 | | 12/2001 | Wakayama et al. |
| 6,660,767 B2 | * | 12/2003 | Jacobs et al. ............... 514/457 |
| 2002/0016533 A1 | * | 2/2002 | Marchitto et al. .......... 600/310 |
| 2002/0115599 A1 | * | 8/2002 | Vernos et al. ................. 514/12 |
| 2002/0160470 A1 | * | 10/2002 | Zhang ..................... 435/173.1 |

\* cited by examiner

Primary Examiner—Bhavesh M. Mehta
Assistant Examiner—Barry Choobin
(74) Attorney, Agent, or Firm—Cohen, Pontani, Lieberman & Pavane

(57) ABSTRACT

The developmental potential of a mammalian oocyte for successful implantation is evaluated by producing a plurality of intensity images of the oocyte using polarized light optics, and calculating a retardance image with a sensitivity of 3 nm or less. The presence, location and morphological characteristics of a meiotic spindle in the oocyte can then be determined based on the spindle structure in the retardance image, and the developmental potential of the oocyte can be evaluated.

10 Claims, 6 Drawing Sheets

MEIOTIC SPINDLE IMAGING IN OOCYTES AND USES THEREFOR IN IN VITRO FERTILIZATION

RELATED APPLICATIONS

This application claims priority from U.S. Provisional Application No. 60/213,750 filed Jun. 23, 2000, the entire contents of which are incorporated herein by reference, including the appendices.

BACKGROUND OF THE INVENTION

1. Field of the Invention

This invention relates to in vitro fertilization (IVF) and to cloning of animals, and to methods for improving the efficiency of IVF and cloning as well as increasing fertilization rates in IVF 2. Description of the Related Art Reproductive wastage is a universal characteristic of biology, with all forms of life devoting enormous energies toward production of germ cells far in excess of the number that eventually develop into a new adult capable of repeating the life cycle. Ovaries of mammals, including women and domestic animal species, contain hundreds of thousands of germ cells at birth, the majority of which never are ovulated, being lost by atretic processes at various stages of follicle development, before puberty or in adult life.

Understanding the basic mechanisms that control the natural selection of the relatively few oocytes that are ovulated, can provide the key to tapping this enormous genetic resource. Applied to women, this knowledge will produce new insights into causes of ovarian dysfunction, and can possibly lead to improved procedures for the diagnosis of infertility, and reduce the risk of high multiple gestations generated by empiric infertility therapies.

Multiple gestations are increasing at an alarming rate due to the growing use of infertility treatments. Presently, 77% of triplets result from assisted reproduction technologies (ART's). Between 1980 and 1994, 10% of the 37,514 triplets, quadruplets, and other-higher multiplies died in their first year, according to the National Center for Health Statistics (Belluck, 1998). Multiple pregnancies suffer a five fold higher stillbirth rate than singleton pregnancies. Of those that survive, 92% are born prematurely and below normal birth weight, which can lead to health and developmental problems. Triplets are twice as likely to develop blindness, mental retardation or seizure disorders as singletons (Belluck, 1998). The rate of cerebral palsy in multiple gestation is 12 times that of singleton pregnancies (Crether, 1993). In a study of 13,206 pregnancies at a Boston hospital, the average cost for postpartum care of triplets was $109,000 (Callahan, 1994).

Theoretically, culture to the blastocyst stage of development would enable embryos to self-select. This technique has proved valuable to selected patients who produce large numbers of healthy-appearing embryos (Meldrum. 1998), which are likely to tolerate the additional days in culture. However, with the increase in the average age of women undergoing IVF, who exhibit less robust responses to controlled ovarian stimulation, blastocyst transfer has less clear value. In this patient group, the majority of embryos do not survive five days in culture, and the embryos which do survive may not exhibit superior implantation rates compared to embryos transferred on the conventional third day. Moreover, even cases of blastocyst transfer present the dilemma of which blastocysts to transfer.

Most clinical embryo viability scoring systems currently used in IVF laboratories focus on embryo morphology. However, because the oocyte serves as the "stem cell" for the embryo, and because more than 80% of aneuploidies that appear in preimplantation embryos originate in the oocyte spindle structure, the evaluation of oocyte structure and determination of fertilization and developmental potential is important, and examination of an important structure in oocytes, the meiotic spindle, is key.

Evaluation of oocyte quality has been difficult in humans. Attempts to estimate oocyte development potential demonstrate a number of morphologic features associated with poor developmental potential, such as darkness, granularity, vacuoles, fragmentation and irregularity (Bolton, 1989, Weimer, 1993, Riley, 1991, Fleming, 1982), but in fact, such standard imaging techniques do not provide a sensitive method of diagnosing oocyte dysfunction. Moreover, the pathobiological basis of these morphological markers is unclear.

IVF offers the opportunity to study the role of the meiotic spindle in human oocyte developmental potential, because oocytes are ovulated at the MII stage of development, when the chromosomes are poised on the metaphase plate, tethered by microtubules that are inherently unstable, and relative to other structures in the oocyte, highly birefringent. In patients who undergo immature oocyte retrieval and IVM, the MI spindle also is available for analysis. Unfortunately, the imaging methods currently used in the IVE laboratory, e.g., Hoffmnan, Nomarski or bright field microscopy, cannot image clearly the meiotic spindle.

A previous study (Battaglia, 1996) compared spindles of oocytes from two groups of women, aged 20 to 25, and aged 40 to 45 years using immunofluorescence and high-resolution, confocal microscopy, and found that meiotic spindles from older women exhibited significantly more abnormalities in chromosome placement and structure. In the older group, 79% of oocytes from the older group exhibited abnormal spindle structure, including abnormal tubulin placement and displacement of one or more chromosomes from the metaphase plate. In the younger group, only 17% exhibited such abnormalities. Spindles in the younger group appeared well ordered, and held chromosomes aligned on the metaphase plate. This data suggests that the architecture of the meiotic spindle is altered in older women, possibly explaining their higher prevalence of aneuploidy.

While intriguing, these results originated from experiments that destroyed the oocytes by fixing and staining them and illuminating them with intense, high frequency light. Moreover, because it employed invasive imaging, it could not link spindle architecture to developmental outcome.

Oocytes, like most living cells, are almost entirely translucent when viewed with a standard optical microscope, making it necessary to employ methods for creating and enhancing contrast in order to discern cellular components. Nomarksi (also called differential interference contrast or DIC), Hoffman, phase contrast, and traditional polarized light techniques use optical interference effects to create contrast, while other imaging methods require marking specific cellular components with exogenous, absorptive colored stains or fluorescent labels. While producing high spatial resolution, these latter methods either kill the cell or affect its function, and therefore, provide limited value to clinical and/or developmental studies.

Birefringence is an optical property that derives from the molecular order found in such macromolecules as membranes, microtubules, microfilaments, and other cytoskeletal components. Polarized light microscopy has the unique potential to visualize and measure birefringent structures, such as spindles dynamically and non-destructively in living cells. However, the low sensitivity of conventional polarized light microscopes makes them marginally suitable for application to mammalian experimental and clinical embryology. (Oldenbourg. 1995, Oldenbourg. 1996. Oldenbourg 1997). In polarized light microscopy, birefringence is measured as retardance which arises when the optical paths between two orthogonal, polarized light beams are differentially slowed as they pass through highly ordered molecules, such as microtubules within the specimen. Birefringent objects, such as spindles, present differences in the paths encountered by polarized light beams as they pass through the object. Compared to non-biological materials, the birefringence of biological samples is weak, only a few nanometers, so the relatively low level of birefringence in biological specimens requires the use of manually-adjusted compensators and rotating stages, a complicated procedure which is prohibitively slow for clinical applications. Moreover, the quantification of retardance levels, necessary to compare spindles, is complicated with conventional polarized light microscopes because the signal achieved originates from both the inherent birefringence in the specimen and the setting of the manually adjusted compensation and analyzers.

SUMMARY OF THE INVENTION

The invention is based, at least in part, on the discovery that meiotic spindles in living mammalian oocytes, in particular living human oocytes, can be imaged non-invasively and without damage. In one embodiment, imaging of oocytes is achieved using an orientation-independent polarized light microscope referred to herein as a "polscope". The polscope uses digital image processing to improve sensitivity, and nearly circularly polarized light combined with electro optical hardware to achieve orientation independence. CCD technology, liquid-crystal compensator optics, and computer algorithms are used to quantify birefringence magnitude (called retardance) and orientation (called azimuth) at every image point in the field of view. The polscope's orientation-independence enables quantification of retardance magnitude and azimuth of spindle fibers within microtubules, because differences in these parameters result from the tissue itself rather than settings of the compensators and stages. The polscope is described in, e.g., U.S. Pat. No. 5,521,705, which is incorporated herein by reference. A method of measuring retardance using this polscope is disclosed in U.S. application Ser. No. 09/883,602 filed on Jun. 18, 2001, also incorporated herein by reference.

At the time of ovulation, the mammalian egg is arrested at metaphase II of the meiotic cell cycle, when the chromosomes are tethered by microtubule fibers of the mejotic spindle. During meiosis and fertilization the meiotic spindles are responsible for proper separation of the nuclear material, and abnormalities in this fragile structure can lead to infertility, miscarriage and genetic diseases, such as Downs Syndrome.

Imaging the meiotic spindle in the unfertilized human oocyte offers a unique opportunity to assess the oocyte's development potential, because up to 80% of aneuploidies found in embryos have their origin in the oocyte and early evidence suggests that the physical state of the spindle reflects its function. Moreover, increased maternal age, the single most important predictor of female fertility, is associated with disruption of the spindle architecture (Battagalia et al., 1996).

Conventional methods of imaging the spindle (e.g. fluorescence labeling techniques) are invasive and not compatible with clinical use. On the other hand, a new orientation-independent polarized light microscope the polscope reveals the spindle's architecture non-invasively. Instead of using exogenous dyes or exposure to damaging levels of light, the polscope measures a fundamental optical property of molecules, called birefringence. Importantly, birefringence enables the non-invasive imaging of the egg spindle due to the molecular order of its microtubules. Subproject I proposes to capitalize on this novel method of imaging meiotic spindles, whose application to mammalian embryology was pioneered by our group, to:

The first aim is to examine whether spindle birefringence can predict oocyte developmental ability. This will be accomplished by capturing polscope images of human MII oocytes from infertile patients undergoing ICSI treatment, and polscope images of MI and II spindles from infertile patients undergoing in vitro maturation (IVM) and ICSI for clinical indications. After imaging, oocytes will be inseminated by ICSI and zygotes from oocytes with or without birefringent spindles will be cultured separately until embryo transfer. Development (fertilization, embryo development, implantation and pregnancy rates) between oocytes with or without spindles will be compared.

The second aim is to examine whether birefringence of MI and MII spindles predicts aneuploidy in IVM human oocytes. Birefringence of MI and MII spindles will be imaged with the polscope during IVM of human oocytes. The presence, shape and maximum retardance of spindles will be measured by the polscope and analyzed by image analysis. After imaging with the polscope, first polar body biopsy and multiprobe fluorescence in situ hybridization (FISH) will be performed on the first polar bodies, to examine the relationship between spindle structure and birefringence, and aneuploidy.

The third aim is to examine whether spindles can be used to optimize the efficiency of IVM conditions, and therefore establish a more effective IVM technique for human IVF. Spindle birefringence will be compared between oocytes matured in vivo (collected from gonadotropinstimulated patients) and oocytes matured in vitro, then the effects of various culture constituents on spindle structure will be determined.

Thus, the invention is directed to determining the presence, position, and morphological characteristics of meiotic spindles in living mammalian oocytes, especially human oocytes by detecting and measuring, non-invasively, and without detriment to the oocytes, the birefringence of the meiotic spindles. Accordingly, in one embodiment, the invention is a method for imaging the meiotic spindle in a living oocyte by detecting birefringence of the meiotic spindle. In another embodiment, the invention is a method for evaluating developmental potential (likelihood of fertilization, embryo development implantation and pregnancy rates) of oocytes by detecting and quantifying the birefringence of the meiotic spindles in the oocytes to determine the presence, position and/or morphology of the spindles. In yet another embodiment, the invention is a method for increasing the fertility rates of oocytes in IVF procedures by detecting the presence and position of the meiotic spindle in oocytes. In still embodiment, the invention is a method of predicting oocyte aneuploidy. In another embodiment, the invention is a method for optimizing IVF conditions, for example temperature conditions for handling of oocytes during IVF, culture and implantation to increase efficiency of IVF and likelihood of fertilization, implantation and embryonic development. In related embodiments, the invention is a non-invasive method for enucleation of mammalian oocytes.

DETAILED DESCRIPTION OF THE PRESENTLY PREFERRED EMBODIMENTS

Figure 1A:
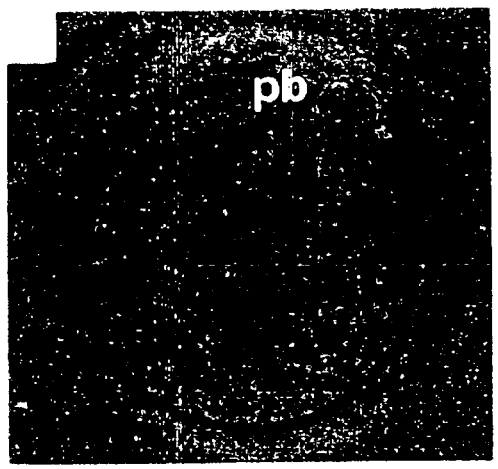
FIGS. 1A and 1B are DIC images of human eggs.
Figure 1B:
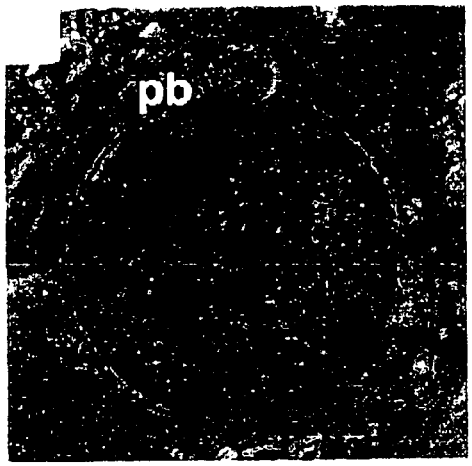
Figure 1C:
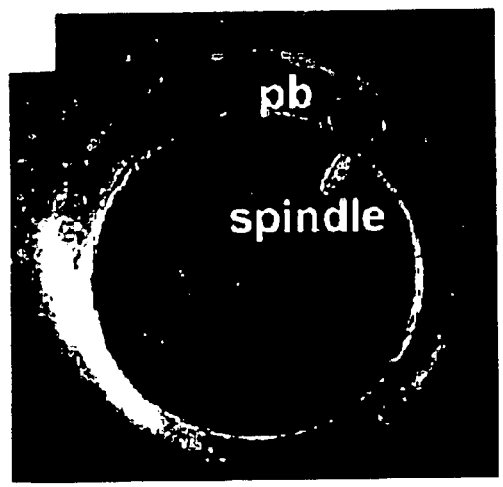
FIGS. 1C and 1D are polscope images of human eggs.
Figure 1D:

The polscope uses digital image processing to improve its sensitivity, and nearly circularly polarized light combined with electro optical hardware to achieve orientation independence. CCD technology, liquid-crystal compensator optics, and computer algorithms are used to quantify birefringence magnitude (called retardance) and orientation (called azimuth) at every image point in the field of view. The polscope's orientation-independence enables quantification of retardance magnitude and azimuth of spindle fibers within microtubules because differences in these parameters results from the tissue itself rather than settings of the compensators and stages. The polscope has been described previously, however, since its application to mammalian embryology is still in its infancy it will be reviewed briefly here.

To produce a retardance image, the polscope generates four intensity images (which are in perfect register because there are no moving parts) at four liquid crystal compensator settings. This gives four numbers at each pixel of the 480×640 pixel image. These four values are used in a ratiometric calculation to determine the sample's retardance and azimuth at each pixel. An additional four images, without the sample in the optical field, are taken to serve as a background correction. Quantification of the specimen's retardance then can be carried out by grayscale thresholding. With this strategy, the polscope can measure retardances of as little as 0.05 nm or 0.03 degrees of phase change (which corresponds to $10^{-4}$ wavelengths of light). In comparison, conventional polarized light techniques have a retardance sensitivity limit of 5 to 10 nanometers, which is barely enough to image the meiotic spindle, of the mammalian oocytes which has a retardance of approximately 3 nm in mouse oocytes. Moreover, since it illuminates specimens with the same intensity of light as DIC, and since DIC, which also employs a form of polarized light, has been used safely during IVF for over 20 years, the polscope is nonroxic to oocytes. Indeed, we have demonstrated experimentally nondetrimental effects on mouse or human oocytes or on mouse embryo developmental potential from exposure to the polscope, so the polscope has the potential for safe application to human IVF as shown in FIG. 1. We also found that human oocytes could be separated into two groups based on the presence of a birefringent spindle.

The polscope has been adapted for use in mammalian embryology. First, the optical path of the polscope for imaging with an inverted microscope was optimized. A number of unique features of oocyte morphology were observed, including a laminar structure of the zona pellucida, as well as the meiotic spindle (Keefe, 1997, Silva. 1997) of mouse and hamster oocytes with our polscope at the Women and Infants Laboratory for Reproductive Medicine at the Woods Hole Marine Biological Laboratory. The safety of polscope imaging in animals was established, a second polscope in our IVF clinic at Women and Infants to study human oocytes and embryos.

Preliminary Data

1. The Mammalian Spindle is Sensitive to Temperature

Rationale: Studies using immunofluorescence labeling have shown that spindles in mammalian oocytes are highly sensitive to perturbations of temperature (Pickering. 1990). The polscope's noninvasive feature allows us to examine the same spindle over time to be able to study the kinetics of spindle polymerization and depolymerization. Results: As little as a 4° C. drop in temperature completely depolymerizes the MII spindle of hamster oocytes within six minutes. While transient exposure to cool temperatures allowed repolymerization upon return to physiological temperatures, prolonged (>6 minutes) exposure to 33° C. did not allow repolymerization. These findings have lead to changes in how eggs are handled in IVF laboratories to ensure that the egg temperature is maintained constantly at 37° C. Discussion: This finding suggests that the spindle can be used as an internal record of the thermal history of the egg.

Meiotic spindles are formed from microtubules comprised of polymerized tubulin and are exquisitely temperature-sensitive. When an orientation-independent polarized light microscope (Polscope, CRI, Cambridge, Mass.) was used to image spindles non-invasively during human ICSI, a high proportion of oocytes exhibited abnormal or missing spindles and oocytes with abnormal spindles had decreased fertilization rates (Abstract #1, ASRM Annual Meeting, October 1999).

Because during handling for IVF and ICSI the Qocytes's temperature can drop transiently, a thermistor to was used to measure temperature near the oocyte and thermal control with a conventional heating stage and a novel heating stage were compared. The Delta T Bioptics, Butler, Pa. uses an indium tin oxide-coated coverslip and a thermostat to precisely regulate the temperature at the oocyte. Egg temperature was also compared using the Delta T Bioptics unit with and without heating the 40 X objective with the Bioptics objective lens warmer. Also compared were spindle integrity, fertilization and clinical pregnancy rates with the three heating systems: a conventional heating plate (HP) (52 cycles, 433 eggs), Delta T Bioptics without objective lens heater (B) (40 cycles, 402 eggs), and Delta T Bioptics with objective lens heater (BR) (29 cycles, 298 eggs).

Results: There were no differences in the average ages, d. 3 FSH levels, or number of previous cycles among the groups. BR provided the most rigorous thermal control to the oocyte (37+/−0.1 C) compared to B (37+/−3 C) or HP (37+/−4 C). Using B, when the unheated objective approached the dish, the Qocyte's temperature dropped 3 C. The rigorous thermal control produced by BH produced a significantly higher rate of normal spindles ($p<0.05$) when compared to oocytes imaged with B (the polscope cannot image spindles with HP) and higher fertilization and clinical pregnancy rates ($p<0.05$) than on cycles using either HP or B.

|    | Spindle (% eggs) | Fertilization Rate (% eggs) | Pregnancy Rate (% cycles) |
|----|------|------|------|
| HP | NA   | 64   | 23.1 |
| B  | 61.4 | 56.7 | 25   |
| BH | 81.2 | 78.8 | 51.7 |

Conclusion: The rigorous thermal control produced by a novel heating system stabilized spindles and increased the fertilization and clinical pregnancy rates achieved after ICSI. Without the objective heater, the objective lens at ambient temperature cooled the egg as it was brought into focus, even when the dish itself was warmed The objective heater overcame this heat sink effect of the objective lens and stabilized the oocyte's temperature. Although microtubules can repolymerize after transient cooling, presumably the function of the reconstituted spindles can be disrupted, since the resulting pregnancy rates were half those produced by rigorous thermal control during ICSI. Imaging the mejotic spindle with the polscope provides an intracellular thermostat during ICSI.

2. The Polar Body does not Predict the Location of the Meiotic Spindle

Rationale: Initial observations of the meiotic spindle in living hamster and mouse oocytes with the polscope suggested that it might not always be located close to the first polar body. Conventional Hoffman or Nomarski contrast reveal the position of the polar body, but not the meiotic spindle. Most immunofluorescent studies of the mammalian meiotic spindle first digest the zona to enhance antibody penetration, and therefore lose the ability to establish the relationship between these important structures. Since clinical embryologists use the polar body to orient the injection side during ICSI this question has clinical importance.

Method: To test the generalizability of these observations, the location of the spindle relative to the polar body with the polscope in oocytes from hamster, mouse, and humans was examined. Oocytes were adjusted until the first polar body and spindle appeared in the same optical plane. Pol images were saved and the angle formed between these two structures calculated by Metamorph (Universal Imaging, Chester, Pa.).

Figure 2A:
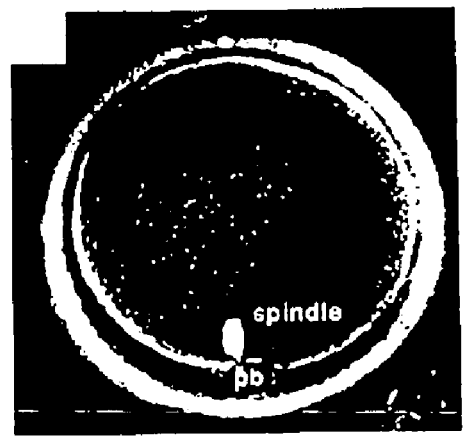
FIGS. 2A–2C are polscope images demonstrating meiotic spindle separated from the polar body in living human eggs.
Figure 2B:
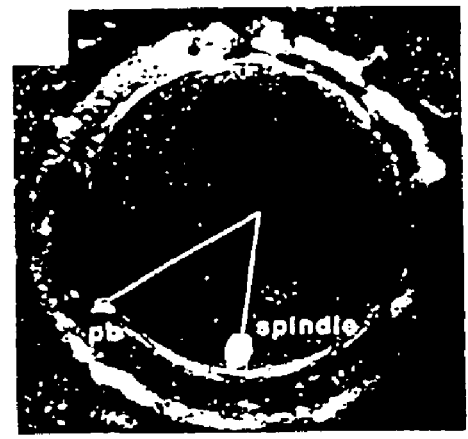
Figure 2C:

Results: Using the polscope, it was found that the polar body does not predict accurately the location of the meiotic spindle in mouse, hamster and human eggs (See FIG. 2). (Silva, 1997) In only 5 of 18 hamster eggs did the polar body accurately predict the placement of the meiotic spindle. For approximately 30% of the eggs, if the polar body had been used as marker, the needle could have disrupted the meiotic spindle.

Discussion: The lack of a close relationship between the spindle and the polar body in MII oocytes raises the question of whether the oocytes should be oriented on the holding pipette based on the location of the spindle rather than of the polar body. It also introduces the question of to what extent "oocyte dysfunction" identified in some oocytes results from iatrogenic rather than inherent factors. While the risk of injury to chromosomes during needle insertion is small, because the needle itself is small relative to the egg, injury would be more likely to occur when the oocyte's cytoplasm is aspirated just before the sperm is injected.

3. The Zona Pellucida has a Multilaminar Structure

Figure 3A:
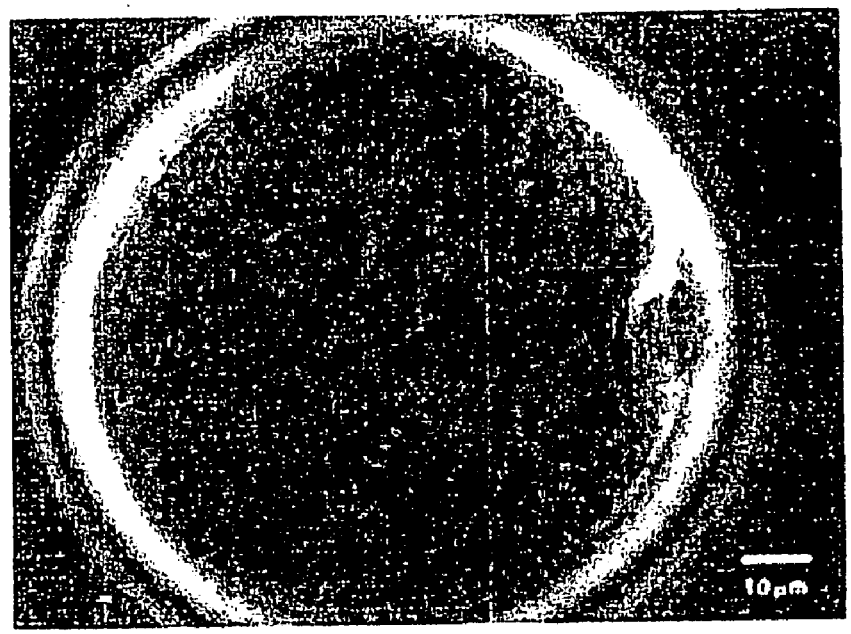
FIGS. 3A and 3B are polscope images of hamster eggs.
Figure 3B:

Rationale: Since the zona pellucida is comprised of three related, filamentous glycoproteins (ZP 1. ZP2, ZP3) it was hypothesized that it would exhibit a high level of birefringence. The impairment of hatching identified in embryos after in vitro culture also begged the question of whether the artificial conditions associated with IVF might change the biophysical properties of zona proteins and thus alter the retardance and/or azimuth. Results: When imaged under Hoffman or Nomarski optics, the zona pellucida appears as a uniform, thick layer. However, when imaged with the polscope, the zona exhibits a multilaminar structure, with three layers differing in their degree of retardance and orientation (See FIGS. 3). Moreover, when embryos were cultured in vitro or in-vivo, the polscope revealed that in vitro culture embryos exhibited impaired thinning of the inner layer of the zone Discussion: Culturing embryos appears to disrupt the normal process of zona thinning by selectively affecting the inner layer of the zona, visible only with the polscope. (Silva, 1997)

4. The Polscope does not Disrupt Pre-implantation Mouse Embryo Development

Rationale: Since the polscope uses light of approximately the same intensity as DIG and Hoffman and since DIG uses plane polarized light with no detrimental effects on embryo development, the polscope appeared to be safe for embryos. Nonetheless, this needed to be established empirically.

Methods: The implantation rate of mice embryos that had been imaged with the polscope were compared to control embryos that were not viewed with the polscope, after transfer into the uterus of pseudopregnant young recipients. Results: Results confirm that the light exposure levels encountered during polscope operation have no apparent affect on blastocyst rate, cell number or pregnancy rates after transfer.

5. Spindle Observation in Living Human Eggs with Polarized Microscope

Rationale: Because spindles imaged by immunofluorescence of human eggs appear to be smaller than mouse, it was necessary to determine whether the polscope could image spindle in human oocytes.

Methods: Spindles from human oocytes aspirated from stimulated ovaries of consenting patients undergoing oocyte retrieval for ICSI were examined. Five hundred and thirty-three oocytes from 51 cycles were examined by the polscope.

Results: Spindles were imaged in 61.4% of the oocytes. After ICSI, more (61.8%; $p<0.05$) oocytes with spindles were fertilized normally, forming 2 pd.

6. Human Oocytes are not Disrupted by Imaging with the Polscope

Rationale: Confirm that the polscope was equally safe for human oocytes.

Method: A observational study to examine whether the polscope is detrimental to human eggs was conducted. Results: The average age was 33.3±3.9 for the patients whose oocytes were exposed to the polscope and 34.7±3.7 for the patients~~'hose oocytes were not exposed to the polscope. Three hundred and thirty seven oocytes from 35 cycles were examined with the polscope, and spindles were imaged in 59.3% of the oocytes. After ICSI, more (74.5%; $p<0.01$) oocytes with spindles were fertilized than oocytes without spindles (44.5%). The total fertilization rate was 62.3% which was the same as the fertilization rate (64.0%) of oocytes (433 from 52 cycles) without being exposed to the polscope. The rate of viable embryos (57.1 %) from the oocytes that had been exposed to the polscope was not statistically different from those of oocytes that had not been exposed to the polscope (59.6%).These results indicate that exposure of human oocyte to polscope for spindle images is not detrimental to oocytes.

Figure 4A:
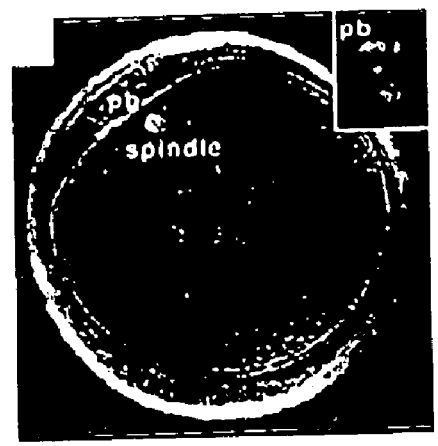
FIGS. 4A–4C shown sequence of aged eggs on post retrieval days 1, 2 and 3.
Figure 4B:
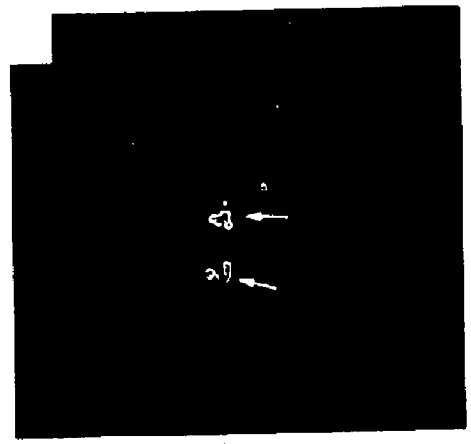

7. Comparison of Polscope and Confocal Microscope Images of Spindles from Human Oocytes.
Rationale: Since the polscope measures spindle retardance and confocal immunocytochemical directly images microtubules, we needed to know to what extent the two methods differed.
Method: We examined spindle images by both polscope and confocal microscopes. Two sources of oocytes were used. One was from unfertilized oocytes on day 1–4 after IVF or ICSI. The other was from maturation of immature oocytes from ICSI patients.
Results: On day 1, in 73% oocytes, spindles could be imaged (FIG. 4A) but spindles in aged oocytes were shorter (8.08±0.84 $\mu$m) than in fresh oocytes (11.2±3.4 nm). Spindle structure obtained with the polscope was comparable to that imaged by confocal microscopy, however, in 27% oocytes on day 1, and all oocytes from days 2–4, no birefringent spindles could be imaged by the polscope. The images obtained by confocal microscopy indicated that spindle was disassembled in these eggs (FIGS. 4B & C). Chromosomes did not align on the center of spindles or were scattered throughout the cytoplasm (FIGS. 4B & C) in aged oocytes.

Figure 5A:
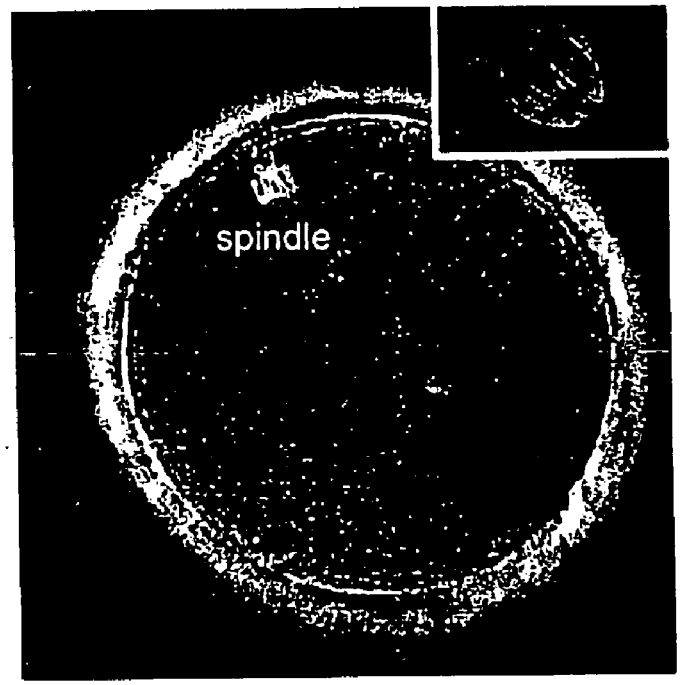
FIGS. 5A and 5B show spindle images during metaphase I and metaphase II after in vitro fertilization.
Figure 5B:
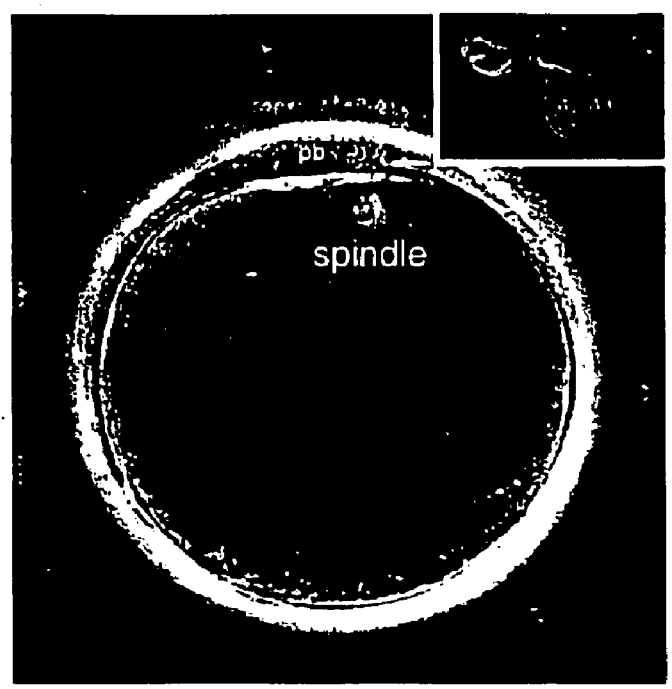

After culture of immature oocytes, most oocytes that reached M-I and M-II had spindles (FIG. 5). When the oocytes with birefringent spindle were fixed and examined by confocal microscopy, it was found that 75% of the oocytes at M-I and 71 % of the oocytes at M-II had typical metaphase spindles with two polars. Most oocytes (75%) with birefringent spindle had normal chromosome configuration, which was conformed by a series of confocal microscopic images. However, oocytes without a birefringent spindle and 25% of oocytes with a birefringent spindle were abnormal and chromosomes were not configured normally. Discussion: The polscope images of spindles are nearly identical to images generated confocal microscope. Thus, the polscope provides nearly the same information about spindle structure as that by confocal microscope, but without damage of the oocytes.

Figure 4C:

Spindle microtubules can be qualified by retardance measurements.
Rationale: During oocyte aging the spindle structure may deteriorate since retardance even in a single microtubule can be quantified. Methods: We measured the retardance in human spindles (as shown in FIG. 4) and found results that large differences in retardance among eggs. Aged oocytes have small spindles and with less birefringence.
Discussion: The quantity of spindle birefringence may be used to monitor oocyte quality or cytoplasmic maturation. These results indicate that spindle retardance can be qualified in living human eggs and that retardance may be an important parameter for evaluation of oocyte quality and to predict cytoplasmic maturation.
Rationale: IVM may be of value to avoid ovarian hyperstimulation in gonadotropin-sensitive patients.

9. In Vitro Maturation of Human Oocytes Aspirated from IVF Patients.
Methods: We cultured immature human oocytes retrieved from stimulated ovaries of consenting patients undergoing oocyte retrieval for ICSI. In vitro maturation was conducted in P1 medium supplemented with 10% SSS at 37 C, 5% C02 in air with 100% humidity.
Results: When 35 oocytes were cultured for 22–24 h (from retrieval), 27(77.1%) released the first polar body and reached metaphase II stage, 17.1%, 2.9% and 2.9% of oocytes were still at metaphase I, GV stage and degenerated, respectively.
Discussion: These results indicate that most immature oocytes can undergo nuclear maturation in vitro in a simple medium, but whether these oocytes developed normal meiotic spindles is unclear.

Research Design and Methods:
Specific Aim 1. Determine whether spindle birefringence, measured with the polscope, can predict subsequent preimplantation embryo development and pregnancy rates.
Rationale: Preliminary results suggest that spindle retardance can be qualified in living human eggs and that it may serve as an important parameter for evaluation of oocyte quality and to predict embryo development potential after fertilization.
Methods: Study sample: Over the five years of this project up to 20,000 oocytes from about 1800 ICSI cycles performed on 600–700 women will be imaged with the polscope attached to the ICSI workstation at Women and Infant Hospital's IVF center (sample size calculated based on an average of 11 oocytes per cycle, 360 ICSI cycles per year for five years, 90% consistent rate). The broad sample of women of different ages (approximately ⅙th of the patients are younger than 30, ⅓rd are between 30 and 35, ⅓rd between 35 to 39, and ⅙th over 40) will provide an opportunity to compare the predictive power of spindle birefringence to maternal age, currently the variable most predictive of IVF outcome. Polscope imaging. After consent is obtained from the couple, polscope images will be acquired of each oocyte prior to ICSI. Since our preliminary data suggest that a significant portion (up to 20–40% of human MII eggs prepared for ICSI) do not exhibit measurable spindle retardance, the first study will determine whether the presence of a spindle itself predicts developmental potential of the resulting embryos. Oocytes will be separated based on the presence of absence of a spindle and the rates of development will be compared between the two groups.

Figure 6A:
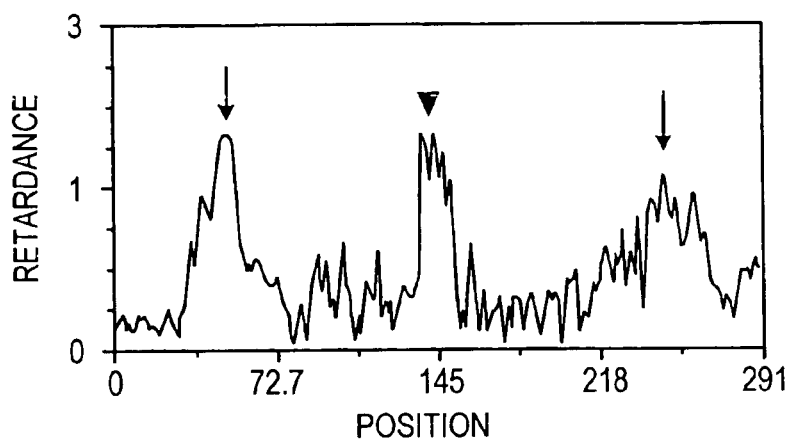
FIGS. 6A and 6B show retardance vs. position in the spindle of a human metaphase II oocyte, along lines A and B in FIG. 6C.
Figure 6B:
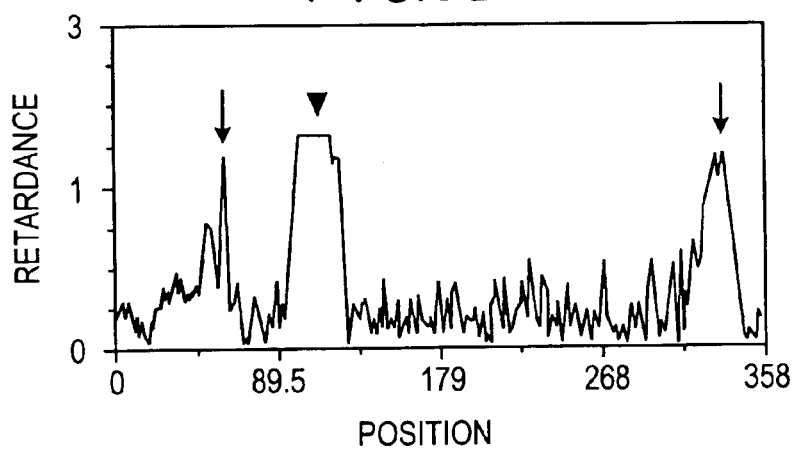
Figure 6C:
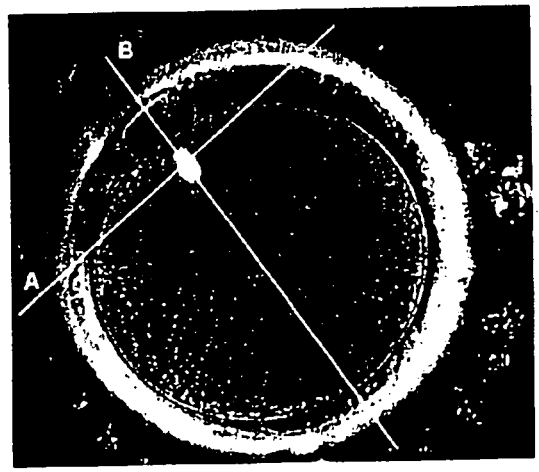

Next, oocytes exhibiting spindle birefringence will be graded morphometrically to determine whether the morphometric features of the spindles, characterized by Battaglia et al. in his study of immunofluorescently-labeled spindles, predict fertilization and embryo developmental potential. To quantify shape by deviation from a standard quantify spindle birefringence morphometrically, we shape (a polygon, such as shown in FIG. 6) aligned with the spindle poles. Measurement will consist of calculating the area between the standard shape perimeter and the perimeter of the spindle, as FIG. 6. Assessment of retardance in the determined interactively by the user with the mouse spindle of a human metaphase II oocyte.

Spindle fiber density will be measured as retardance magnitude (area under the curve) of a line scan drawn across the width and length of the spindle with metamorph. (See FIG. 6.) Length, width, aspect ratio (length/width), symmetry about the metaphase plate, maximum retardance, orientation of spindle's primary axis (azimuth) relative to polar body, and circularity also will be measured. These morphometric tools will be provided by Metamorph image analysis system to measure these descriptors. Retardance magnitude and azimuth are measured automatically by the Polscope software. Location of the spindle within the oocyte relative to the oolemma and the polar body also will be determined by measuring distance observed between the spindle centroid and the oolemma. Images of spindles generated with the polscope will be saved to a Zip Drive for later analysis.

ICSI then will be performed and the resulting zygotes cultured in groups based on the normalcy of their spindles, to day 3. 5, 6, depending on standard clinical protocols. The rates of development in vitro and of implantation, and delivery of term babies after embryo transfer will be compared among groups.

Clinical variables known to affect IVF outcome including age, day 3 FSH level, duration of infertility, smoking history, presence of hydrosalpinges and diagnosis also will be collected from the medical records of consenting patients.

Data Analysis: We will compare mean rates of development between or among groups (i.e. with and without spindles) using multi-level modeling techniques (Hogan and Blazar, 2000). These are analogous to T tests and ANOVA, but make proper adjustment for variability at different levels (i.e. variability of embryos within the same woman; variability across cycles, variability between women). These regression models are generalizations of standard linear and logistic regression models, and are flexible enough to allow examination of interactions between spindle morphometric variables and other, established clinical variables (see e.g. Peach and McGill 1998, Liu et al. 1999, Pratt et al. 1999 for recent uses) and readily available in commercial statistical packages (e.g., S-Plus, Matisoft, 1998). We will evaluate the predictive accuracy, such as the multiple correlation coefficient (Rsquared) and Akaike! 'S Information Criterion (AIC). The pregnancy outcome model will use clinical pregnancy and delivery of viable infant(s) as outcome variables. We will quantify the predictive power of the fitted regression model using the apparent error rate, i.e., the proportion of misclassifications of the original observations using the derived model, after correcting for the bias inherent in this method with a bootstrap estimator (Rencher 1998).

Because multiple embryos are transferred, cycles in which the fate of all embryos is known e.g. two embryos transferred resulted in twins; will be studied in a subanalysis. Logistic regression models will be constructed with and without the polscope morphology data and their predictive power compared. Finally, after developing a prediction model, receiver-operator characterization (ROC) analysis will be performed to determine what cut off points of continuous morphologic variable, optimize sensitivity and specificity of spindle morphology as a predictor of outcome. Power and sample size issues will be accounted for in a post-hoc analysis of the collected data (Cohen 1988). Specifically, using the method provided by Hsieh et al. (1998) we will ask if, given a desired level of statistical power and the observed effect size, a sufficient number of samples was taken of embryo oxygen consumption.

Specific Aim 2: Does spindle birefringence of the metaphase I spindle predict aneuploidy in human oocytes matured in vivo and in vitro?.

Rationale: As the meiotic spindle is important for normal chromosome alignment and separation of maternal chromosome during oocyte nuclear maturation and fertilization, oocytes with abnormal or absent spindles may be predisposed to develop aneuploidy. Therefore, we hypothesize that oocytes without spindles or with structurally abnormal spindles will be more likely to develop aneuploidy than oocytes with structurally normal spindles.

Methods: Ploidy will be determined by polar body biopsy and six probe fluorescent in situ hyhridization (FISH) (chromosomes 22, 21, 18, 16, and 13), Polar body biopsy and FISH have been used widely for preimplantation genetic diagnosis in human IVF clinics. Since polar bodies contain the complementary genotype to the oocyte if the polar body contains abnormal chromosome distribution, it can be concluded that the oocytes also contain abnormal chromosome distribution. Polar bodies are considered an unnecessary by-product of meiosis, so their biopsy does not interfere with the developing embryo itself Since we cannot experiment on embryos, only the 1st polar body will be biopsied 1-however, since about 80% of aneuploidies in the embryo arise in the female, and most of these during MI, these studies may be generalizable to embryo aneuploidy.

Polar Body Biopsy. Only first polar bodies will be biopsied, so as to not breech NIH's embryo guidelines prohibiting invasive research on fertilized oocytes or embryos. To perform polar body biopsy, oocytes are held on a pipette with the polar body at the 12 o'clock position. Using a sharp needle, a slit is made in the zona pellucida tangentially to the polar body. With a thin pipette, the polar bodies are removed from under the zona pellucida and fixed for FISH examination. After the first polar body biopsy, oocytes will be inseminated by ICSI.

FISH Analysis. FISH is a method in which fluorescently labeled chromosome-specific probes are hybridized to metaphase or interphase chromosomes for aneuploidy. The structure of the spindle and it birefringence will be used to classify oocytes into normal and abnormal groups, and the rates of aneuploidy will be compared between groups. Nuclear fluorescent In situ Suppression Hybridization (N-FISH): Slides with affixed polar body cells are passed through three changes of Freshly prepared 3:1 methanol :acetic acid fixative, then treated with 10% fleshly prepared pepsin solution at 37 degrees for five minutes to digest some of the proteins. After protein digestion, cells are fixed for five minutes in 1% formaldehyde, then the lides are soaked in phosphate buffered saline (PBS) for five minutes and dehydrated in an ethanol series (70,8 5 and 100%). A multicolor, five probe mixture for detecting chromosomes 13,21,18.16 and 22 (multivision PB multicolor probe panel, Vysis, downers Groove, 11 is applied to the slide under a coverslip (region where the polar body if attached to the slide) and the probe and the nuclear DNA are denatured simultaneously at 73 degrees in hybrite (Vysis) for two minutes. After denaturation, the cover slip is sealed with rubber cement and incubated at 37 degrees in a humid chamber for approximately 12 to 16 hours (hybridization). After hybridization, the rubber cement and coverslip are carefully removed and the slides are washed in 2×SSC for 10 minutes at 76 degrees. Slides are air dried and counter stained with DAPI and visualized under an epifluorescence microscope with appropriate filters to detect the appropriate signals. Signals are imaged using the Applied Imaging Cytovision system.

Expected results: We expect to find a relationship between spindle structure and bireflingence and normal chromosome segration during MI to MI transition. More polar bodies from oocytes without spindles or with partially-deploymerized spindles, will exhibit aneuploidy than polar bodies from oocytes with spindles. If the results are as expected, the polscope will help predict whether oocytes will develop normally after fertilization.

Specific Aim 3 Can non-invasive imaging of spindle birefringence be used to optimize In Vitro Oocyte maturation of human oocytes?.

Rationale: For conventional infertility treatment by in vitro fertilization, oocytes are collected from gonadotropin-stimulated women. Although protocols for controlled ovarian hyperstimulation for IVF have been used in human IVF clinics for many years, some patients do not tolerate the controlled ovarian hyperstimulation used for IVF. In particular, young women and women with polycystic ovary syndrome (PCOS) are prone to develop severe ovarian hyperstimulation (OHSS), which canconvert an elective fertility procedure into a life-threatening medical condition, involving a hypercoaguable state, renal failure and vascular permeability, as well as significant pain and fear on the part of the patient. Culture of immature oocytes aspirated fi-om the unstimulated ovaries of these women has been proposed as a method of infertility treatment without using exogenous gonadotropins.

Studies in some mammals indicate that modifications in culture media significantly increase the subsequent embryo development and implantation rates, but these enGpoints are difficult to study human embryos. For example studies in pig and cattle indicated that addition of epidermal growth factor (Abeydeera et al., 1998; Harper et al., 1993; Lorenzo et al., 1996; Wang and Niwa, 1995), cysteine (Yoshida et al., 1993; De matos et. al., 1995; 1997), gonadotropins (Funahashi et al., 1993 Harper et al., 1993) and deletion of serum (Funahashi and Day, 1993) improved cytoplasmic maturation of the oocyte. The overall goal of this specific aim is to increase our understanding of how hormones, growth factors anti-oxidants and other in vitro conditions interact to affect the structures of MI and MII spindles of oocytes cultured in vitro for experimental and or clinical indications. Since MI and MII spindle structure are so critical to the fate of the oocyte and embryo, such knowledge will facilitate development of more efficient methods of IVM in humans. We have abundant supplies of immature oocytes retrieved for ICSI, so most experiments will employ oocytes from this source. However, we also have limited access to oocytes being matured in vitro after immature oocyte aspiration for clinical indications. Oocytes that go into generated pregnancies after ICSI and IVE will be used to establish normal controls for spindle structure.

Experiment 1:

Methods: Normal controls: In order to determine whether in vitro matured oocytes exhibit abnormal spindles and whether modifications in the IVM procedure can improve spindle structure, it is important first to establish what normal spindles, derived from successful IVF cycles, look like. Normal MII spindles will be defined as those imaged from vivo matured oocytes which have gone on to generate normal embryos and viable pregnancies after ICSI. We will focus on the subset of pregnancies in which the fates of specific oocytes were embryos was known with certainty e.g. twin or triplet gestations after the transfer of two or three embryos, respectively. Structure of MII spindles from oocytes cultured in vitro will be compared to these "normal", in vivo matured oocytes. It is important to note that gonadotropin stimulation itself may have effects on spindle birefringence, so these controls cannot be assumed to be strictly normal physiologically. Rather, because these oocytes were known to have gone on to generate normal babies, they can be assumed to be normal oocytes generated after gonadotropin stimulation. Despite this distinction, this information will be valuable clinically.

Immature oocytes will be obtained from young and old PCOS and other gonadotropin-sensitive patients who have consented to IVM in order to avoid the controlled ovarian stimulation component used during conventional IVF and from oocytes retrieved at CV stage despite gonadotropin stimulation. For immature oocyte aspiration, patients rather than being stimulated with exogenous gonadotropins, follicles will be synchronized with oral contraceptives, then hCG, according to the protocol published by the McGill group (Chian et al., 1999). Oocytes will be aspirated under low (50–75 mm Hg) pressure and cultured in Tissue Culture Medium (TCM) 199 (Sigma) containing $75_4$ulU/ml LH and FSH, 10% maternal serum or serun-free medium (for details, see below) in organ culture dishes at 37 C, 5% C02 in air. 24–36 h after culture, oocytes will be examined for maturation and their spindles will be imaged with the polscope.

Matured oocytes will be fertilized by (ICSI) as the zona pellucida of eggs becomes hardening during in vitro maturation.

ICSI of in vitro matured oocytes: Oocytes that reach metaphase II (release the first polar body) will be inseminated by ICSI. The ICSI protocol has been used in human IVF clinics for several years world-wide and it is a standard ART technique in our IVF clinic. During the two past years ICSI was performed on just over 40% of the IVF cycles at our center and a 70–80% fertilization has been achieved. Embryo culture, cryopreservation and transfer will follow procedures standard to our IVF laboratory.

Embryo culture and tracking: After ICSI, oocytes with or without normal spindles will be cultured separately in groups of two to three, and fertilization will be examined 6–18 h later. Normally fertilized eggs, with two pronuclei (zygotes) will be cultured in growth medium (P 1 medium with 10% SSS). At Day 3, embryos will be graded and selected for transfer or continued in culture (in blastocyst medium), depending on the numbers of developing embryos, following standard clinical protocols. We find greater than 90% of zygotes cleave and 50% go on to form blastocysts in ICSI patients. Embryo transfer has resulted in an average 30% clinical pregnant rates, with variation about this overall average, depending on age.

Experiment 2. Effects of Serum on Spindle Birefringence of Human Oocytes Cultured in vitro Rationale: In vitro maturation usually is conducted in medium supplemented with maternal serum (Cha and Chian, 1998; Trounson et al., 1994; Groud et al., 1998). Many unknown factors are present in the serum, some probably detrimental to oocyte maturation. In addition, serum usually is collected from the patients themselves, so detrimental circulating factors from the patients, if present, still are present in the serum-treated culture media. Furthermore, it has been found that medium without serum significantly improves cytoplasmic maturation in pig and cattle oocytes (Funahashi and Day, 1993; Harper and Brachett, 1993). Therefore, supplementation of maternal serum in culture medium may be not as good as serum-free medium. In experiment 2 we will test whether maternal serum is beneficial for cytoplasmic maturation in human as compared with serum-free medium.

Methods: Immature oocytes from the same patient will be separately cultured in TCM 199 with maternal serum (10%) or without serum. After maturation, oocytes will be examined by polscope and their spindle structure analyzed and compared to normal controls.

Experiment 3. Effects of Epidermal Growth Factor (EGF) on Spindle Structure in IVM Oocytes Rationale: EGF has been found in follicular fluid in most mammals. The stimulative effects of EGF on oocyte nuclear maturation have been reported in most mammals including humans (Das et al., 1991; Martin et al., 1998). EGF supplementation in oocyte maturation medium may improve the likelihood of normal spindle formation.

Methods: Immature oocytes from the same patients will be cultured in TCM 199 with or without 10 ng/ml EGF (a concentration has been found to stimulate oocyte maturation in mammals tested). After maturation, oocytes will be examined with the polscope and their spindles examined and compared to normal controls.

Experiment 4. Effect of Cysteine on Spindle Structure of Human Oocytes Matured in vitro Rationale: It has been found that intracellular glutathione level is an important marker for successful IVM in some mammals (Abeyderra et al., 1998; De Matos et al., 1995;

1997; Calvin et al., 1986). One of the important roles of glutathione is its protective role on cells as an antioxidant (Meister, 1983). Some evidence suggests that spindle microtubules are targets of attack by ROS. In TCM-199, cysteine has been supplemented but the concentration is too low to provide enough cysteine for synthesis of intracellular glutathione (Yoshida et al., 1993). The addition of cysteine in pig and cattle IVM medium significantly increases the efficiency of IVM.

Methods: Immature oocytes from the sante patient will be cultured in medium with or without 0.6 mM cysteine (a concentration used in culture medium in other animals). After maturation, oocytes will be examined with the polscope and their spindle structure compared to normal cAritrols.

Experiment 5. Maturation of Cumulus-free Immature Oocytes for Rescue Insemination Rationale: In IVF clinics, it has been found that many immature eggs result even from gonadotropin-stimulated patients during ICSI. Typically, these eggs are discarded, as the cumulus already have been removed in preparation for ICSI. Ample evidence suggests that IVM is incomplete in cumulus-free oocytes. Because cumulus cells are important for cytoplasmic maturation of oocytes, after removing cumulus, removed cumulus cells, even they lose the connection with oocytes, still provide beneficial effects on oocyte maturation. Therefore, co-culture of immature oocytes with these cells may improve IVM of human oocytes. In addition, it has been found that cysteamine, which also can be used to synthesize intracellular glutathione in oocytes without cumulus cells, stimulates cytoplasmic maturation in pig and cattle oocytes Yamauchi and Nagai, 1999; De Matos et al., 1995). Thus, supplementation of cysteamine in medium will stimulate intracellular glutathione synthesis and maturation.

Methods: Cumulus cells will be collected and centrifuged to remove associated hyaluronidase in culture medium. Only cumulus cells from the same patient will be used for co-culture. Next, immature oocytes will be cultured in medium with or without cysteamine. After maturation, the spindles in matured oocytes will be examined with the polscope and inseminated by ICSI. Fertilization and embryo development will be compared between two groups. The viable embryos will be transferred to the patients or frozen. Immature oocytes from all ICSI patients For additional disclosure in support of the invention as claimed, see the following papers, attached hereto as appendices A and B, and incorporated herein by reference:

A. CRI, General Program Prize Papers, Sep. 27, 1999 W. H. Wang. R. J. Hackett, L. Meng, D. L. Keefe, Spindle Observation and Its Relationship with Fertilization after ICSI in Living Human Oocytes B. Lin Liu, Rudolf Oldenbourg, James R. Trimarchi, David L. Keefe, A reliable, noninvasive technique for spindle imaging and enucleation of mammalian oocytes, Nature Biotechnology, Vol. 18, February 2000.

What is claimed is:

1. A method of detecting the presence of a meiotic spindle in a mammalian oocyte comprising the following steps:
   producing a plurality of intensity images of the oocyte using polarized-light optics,
   calculating from said plurality of intensity images an image of the retardance at a plurality of points in the oocyte, wherein said retardance image provides a sensitivity of 3 nm of retardance or less, and
   determining the presence or absence of a meiotic spindle in the oocyte based on the presence or absence of a spindle structure in the retardance image.

2. A method of detecting the location of a meiotic spindle in a mammalian oocyte comprising the following steps:
   producing a plurality of intensity images of the oocyte using polarized-light optics,
   calculating from said plurality of intensity images an image of the retardance at a plurality of points in the oocyte, wherein said retardance image provides a sensitivity of 3 nm of retardance or less,
   locating a spindle structure in the retardance image, and
   determining the location of the meiotic spindle in the oocyte based on the location of the spindle structure in the retardance image.

3. A method of determining the morphological characteristics of a meiotic spindle in a mammalian oocyte comprising the following steps:
   producing a plurality of intensity images of the oocyte using polarized-light optics,
   calculating from said plurality of intensity images an image of the retardance at a plurality of points in the oocyte, wherein said retardance image provides a sensitivity of 3 nm of retardance or less,
   locating a spindle structure in the retardance image, and
   determining the morphology of the meiotic spindle based on the morphology of the spindle structure in the retardance image.

4. A method of evaluating the likelihood of fertilization of a mammalian oocyte comprising the following steps:
   producing a plurality of intensity images of the oocyte using polarized-light optics,
   calculating from said plurality of intensity images an image of the retardance at a plurality of points in the oocyte, wherein said retardance image provides a sensitivity of 3 nm of retardance or less,
   determining at least one of the presence, location, and morphological characteristics of a meiotic spindle in the oocyte, based on at least one of the presence, location, and morphological characteristics of a spindle structure in the retardance image of the oocyte, and
   evaluating the likelihood of fertilization based on at least one of the presence, location, and morphological characteristics of the meiotic spindle.

5. A method of evaluating the developmental potential of a mammalian oocyte for one of successful development, implantation, and pregnancy, comprising the following steps:
   producing a plurality of intensity images of the oocyte using polarized-light optics,
   calculating from said plurality of intensity images an image of the retardance at a plurality of points in the oocyte, wherein said retardance image provides a sensitivity of 3 nm of retardance or less,
   determining at least one of the presence, location, and morphological characteristics of a meiotic spindle in the oocyte, based on at least one of the presence, location, and morphological characteristics of a spindle structure in the retardance image of the oocyte, and
   evaluating the developmental potential based on at least one of the presence, location, and morphological characteristics of the meiotic spindle.

6. A method of increasing the fertility rates in mammalian oocytes undergoing in-vitro fertilization procedures, comprising the following steps:
   for each oocyte being considered as a candidate for in-vitro fertilization procedures, producing a plurality of intensity images of the oocyte using polarized-light optics, calculating from said plurality of intensity images an image of the retardance at a plurality of points in the oocyte, wherein said retardance image provides a sensitivity of 3 nm of retardance or less, determining at least one of the presence, location, and morphological characteristics of a meiotic spindle in the oocyte, based on at least one of the presence, location, and morphological characteristics of a spindle structure in the retardance image of the oocyte, and evaluating the likelihood of fertilization based on at least one of the presence, location, and morphological characteristics of the meiotic spindle.

7. A method as in claim 6 further comprising using the evaluation of fertilization likelihood in each candidate oocyte to determine its fitness for use in subsequent procedures including at least one of fertilization, culturing, and implantation.

8. A method of predicting aneuploidy in a mammalian oocyte, comprising the following steps:

producing a plurality of intensity images of the oocyte using polarized-light optics, calculating from said plurality of intensity images an image of the retardance at a plurality of points in the oocyte, wherein said retardance image provides sensitivity 3 nm of retardance or less, determining at least one of the morphological characteristics and total retardance of a meiotic spindle in the oocyte, based on at least one of the morphological characteristics and total retardance of a spindle structure in the retardance image of the oocyte, and evaluating the likelihood of ancuploidy in the oocyte based on at least one of the morphological characteristics and the total retardance of the meiotic spindle.

9. A method for enucleation of mammalian oocytes, comprising the following steps:

providing an oocyte and enucleation apparatus, wherein said enucleation apparatus has a distal end that is brought into contact with the oocyte, using a microscope to provide a viewing field that comprises the oocyte and the distal end of the enucleation apparatus, producing a plurality of intensity images of the viewing field using polarized-light optics, developing from said plurality of intensity images an image of the retardance at every point in the viewing field, wherein said retardance image provides a sensitivity of 3 nm of retardance or less, locating a spindle structure in the retardance image, determining the location of a meiotic spindle within the viewing field from the location of the spindle structure in the retardance image, and using the location of the meiotic spindle to effect at least one of removal of a spindle from an oocyte, and verification that a spindle has been removed from an oocyte.

10. A method for nuclear transfer in mammalian oocytes, comprising the following steps:

providing an oocyte and enucleation apparatus, wherein said enucleation apparatus has a distal end that is brought into contact with the oocyte, using a microscope to provide a viewing field that comprises the oocyte and the distal end of the enucleation apparatus, producing a plurality of intensity images of the viewing field using polarized-light optics, developing from said plurality of intensity images an image of the retardance at every point in the viewing field, wherein said retardance image provides a sensitivity of 3 nm of retardance or less, locating a spindle structure in the retardance image, determining the location of a meiotic spindle within the viewing field from the location of the spindle structure in the retardance image, and using the location of the meiotic spindle to effect at lest one of implantation of a spindle into an oocyte, and verification that a spindle has been implanted into an oocyte.

* * * * *